(12) United States Patent
Williams et al.

(10) Patent No.: US 8,777,064 B2
(45) Date of Patent: Jul. 15, 2014

(54) HAND SANITIZING DOOR OPENER

(76) Inventors: Keith Dawson Williams, Germantown, TN (US); Dawson Allen Williams, Austin, TX (US)

( * ) Notice: Subject to any disclaimer, the term of this patent is extended or adjusted under 35 U.S.C. 154(b) by 113 days.

(21) Appl. No.: 12/896,833

(22) Filed: Oct. 1, 2010

(65) Prior Publication Data

US 2012/0080451 A1   Apr. 5, 2012

(51) Int. Cl.
*B67D 1/07* (2006.01)
*B67D 7/06* (2010.01)

(52) U.S. Cl.
USPC ........... 222/192; 222/181.3; 222/505; 16/412

(58) Field of Classification Search
USPC ............ 222/92, 153.01, 153.04, 153.14, 180, 222/181.1, 181.3, 192, 192.1, 321.8, 505, 222/509; 16/412
See application file for complete search history.

(56) References Cited

U.S. PATENT DOCUMENTS

| | | | |
|---|---|---|---|
| 3,967,478 A | 7/1976 | Guinn | |
| 4,171,776 A | 10/1979 | Pagliaro | |
| 4,644,689 A * | 2/1987 | Arians | 49/70 |
| 4,710,634 A * | 12/1987 | Brookes | 250/455.11 |
| 4,896,144 A | 1/1990 | Bogstad | |
| 5,808,553 A | 9/1998 | Cunningham | |
| 5,882,667 A * | 3/1999 | Jones | 424/405 |
| 6,029,600 A * | 2/2000 | Davis | 116/200 |
| 6,298,521 B1 | 10/2001 | Butterfield | |
| 6,789,695 B1 * | 9/2004 | Gaudreau | 221/102 |
| 6,874,697 B2 | 4/2005 | Callueng | |
| 7,175,807 B1 * | 2/2007 | Jones | 422/24 |
| 7,320,418 B2 * | 1/2008 | Sassoon | 222/649 |
| 7,338,646 B2 * | 3/2008 | Gilbert | 422/292 |
| 7,360,674 B2 * | 4/2008 | Sassoon | 222/649 |
| 7,458,742 B2 | 12/2008 | Stropkay et al. | |
| 7,598,501 B2 * | 10/2009 | Jones | 250/455.11 |
| 7,770,782 B2 | 8/2010 | Sahud | |
| 7,878,371 B2 * | 2/2011 | Sassoon | 222/52 |
| 8,061,565 B1 * | 11/2011 | Baker | 222/192 |
| 8,152,027 B1 * | 4/2012 | Baker | 222/192 |
| 2005/0011042 A1 * | 1/2005 | Hupp et al. | 16/110.1 |
| 2008/0023497 A1 * | 1/2008 | Sassoon | 222/402.11 |

(Continued)

OTHER PUBLICATIONS

Gojo Industries, Inc., Purell® Foaming Hand Sanitizer (2009), www.gojo.com/united-states/productsearch.aspx?ProdID={65D68918-B26B-4E19-9706-29800097299D}, Gojo Industries, Inc. (Akron, Ohio, U.S.A.).

(Continued)

*Primary Examiner* — Kevin P Shaver
*Assistant Examiner* — Patrick M Buechner
(74) *Attorney, Agent, or Firm* — Walker, McKenzie & Walker, P.C.

(57) ABSTRACT

A hand sanitizing apparatus for sanitizing a person's hand while operating a handle of a door opener. The apparatus includes a housing body received about the door opener and limiting access to the handle. A canister of hand sanitizer is received into the housing body, and the canister has a nozzle. The apparatus includes an actuator mounted within the housing body upon an axle for movement from a first position to a second position. The actuator has a hand-contacting portion including a palm-contacting paddle, and the actuator is operably coupled to the nozzle and to the handle. As the actuator is moved from the first to the second position, the handle opens the door as the nozzle dispenses hand sanitizer from the canister.

1 Claim, 4 Drawing Sheets

(56) References Cited

U.S. PATENT DOCUMENTS

| | | | |
|---|---|---|---|
| 2008/0305020 A1* | 12/2008 | Oshmyansky | 422/291 |
| 2009/0071975 A1* | 3/2009 | Stropkay et al. | 222/1 |
| 2009/0265990 A1 | 10/2009 | Stratmann | |
| 2009/0324444 A1 | 12/2009 | Stratmann | |
| 2010/0294806 A1* | 11/2010 | McDowell | 222/173 |

OTHER PUBLICATIONS

Gojo Industries, Inc., Purell® APX™ Aerosol Dispensing System—Dove Gray (2009), www.gojo.com/united-states/productsearch.aspx?ProdID={F2D0A9E8-4098-473F-AD2F-DB19F4564DAA}, Gojo Industries, Inc. (Akron, Ohio, U.S.A.).

* cited by examiner

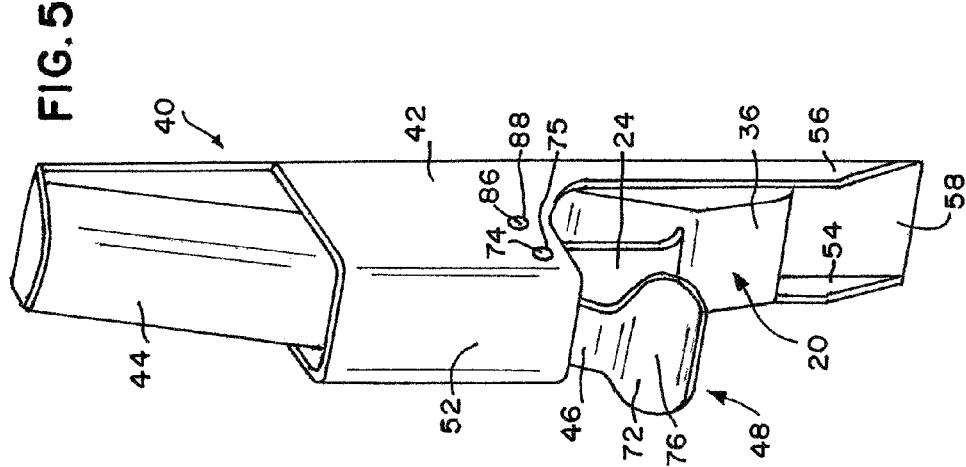
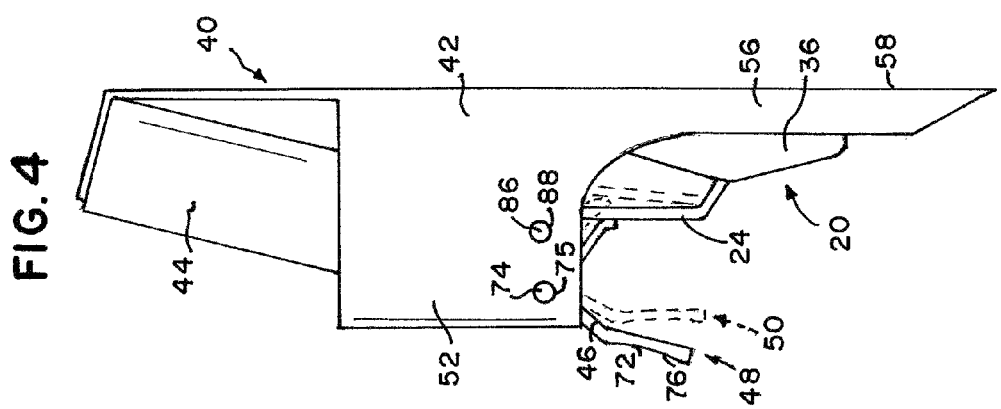
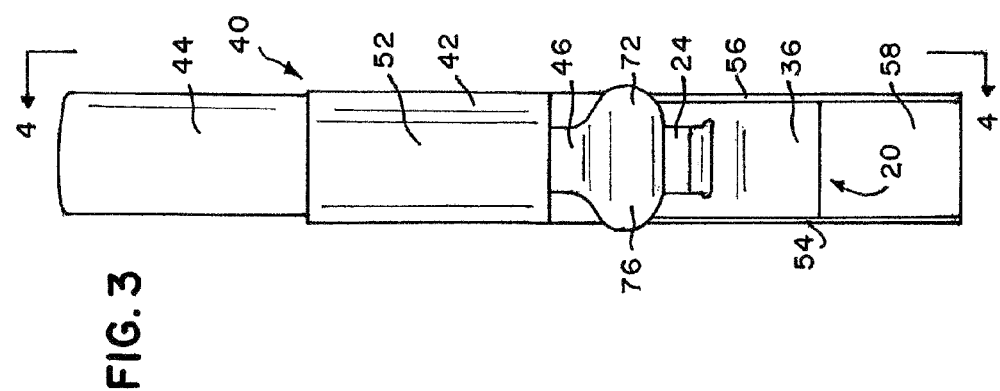

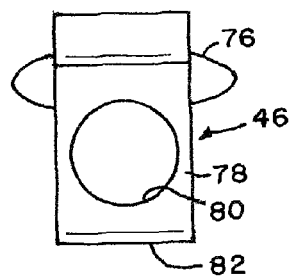
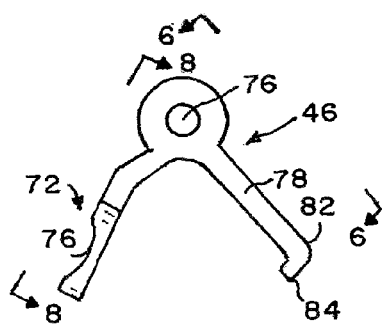
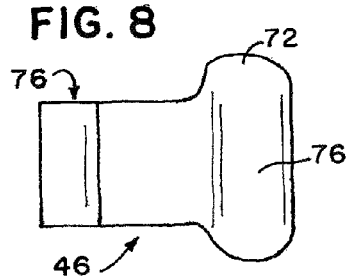
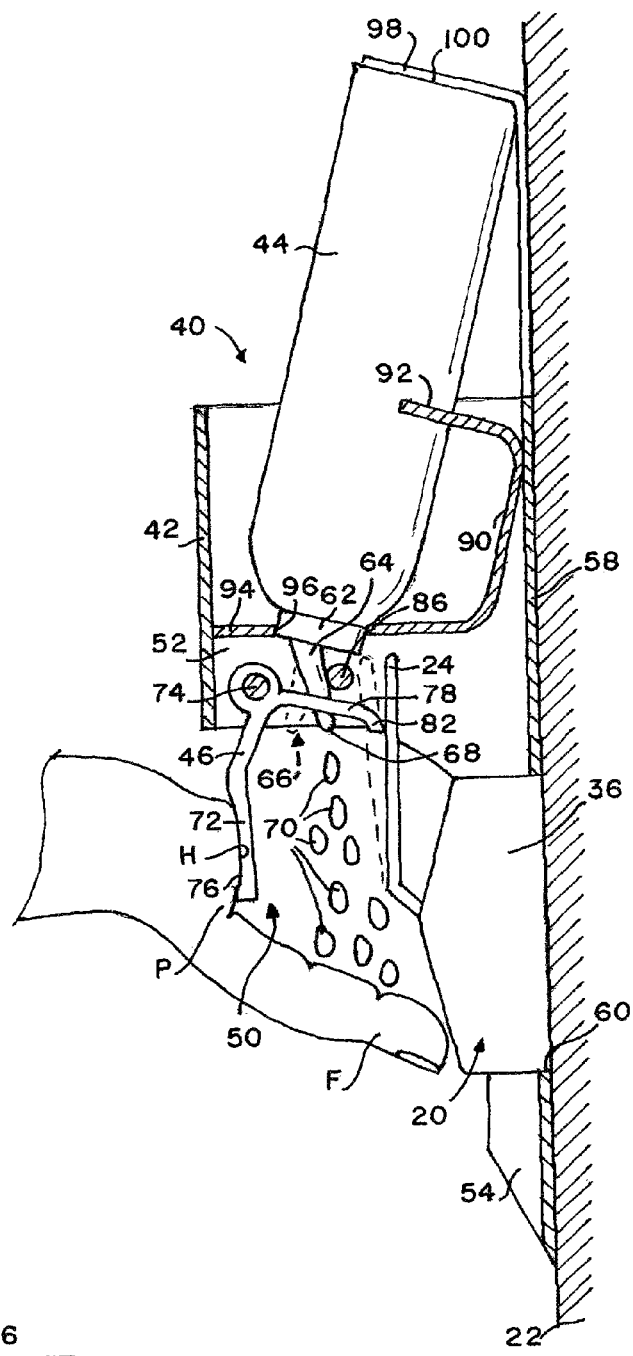

HAND SANITIZING DOOR OPENER

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO COMPACT DISC(S)

Not applicable.

BACKGROUND OF THE INVENTION

1. Field of the Invention

The present invention relates, in general, to door openers and sanitation in a hospital or clinical setting, and in particular, to sanitizing apparatus for sanitizing the hands of a person entering a hospital or clinical room.

2. Information Disclosure Statement

Antibiotic-resistant bacteria, such as methicillin-resistant staphylococcus aureus ("MRSA") are a well-known health problem in hospitals and clinics, and can be passed from patient to patient as health-care providers and visitors touch a succession of surfaces or patients in a hospital or clinic. To solve this problem, hospitals and clinics provide wall-mounted dispensers of hand-sanitizing foam, liquid, or gel, such as PURELL® foaming aerosol dispenser canisters, for each room so that persons entering the room can sanitize their hands. Despite established policies and signs admonishing persons to sanitize their hands frequently, ensuring compliance with such policies is difficult to enforce, and bacteria are thus spread from patient to patient.

It is therefore desirable to have means or apparatus that ensures that hand sanitation occurs each time a person enters a room occupied by a patient, preventing entry to the patient's room unless such hand sanitation has occurred. It is further desirable that such a hand sanitation apparatus be adapted for retrofitting use with existing door openers, allowing existing door openers to become hand sanitizing door openers without modification or drilling, etc., of the existing door openers.

The following patent references are also known regarding disinfecting door opening apparatus: Brookes, U.S. Pat. No. 4,710,634 (issued Dec. 1, 1987); Cunningham, U.S. Pat. No. 5,808,553 (issued Sep. 15, 1998); Butterfield, U.S. Pat. No. 6,298,521 (issued Oct. 9, 2001); Callueng, U.S. Pat. No. 6,874,697 (issued Apr. 5, 2005); Sassoon, U.S. Pat. No. 7,320,418 (issued Jan. 22, 2008); Sassoon, U.S. Pat. No. 7,360,674 (issued Apr. 22, 2008); and Stropkay et al., U.S. Pat. No. 7,458,742 (issued Dec. 2, 2008).

Brookes, U.S. Pat. No. 4,710,634, discloses a sanitizing housing above a door handle, in which the housing holds an ultra-violet germicidal light.

Cunningham, U.S. Pat. No. 5,808,553, describes a circuit and apparatus that keeps a person locked in a restroom until sanitizing steps, including spraying disinfectant soap onto the person's hands, have been completed at the lavatory sink.

Butterfield, U.S. Pat. No. 6,298,521, discloses a circular housing that fits around a door knob shaft, in which sublimed disinfectant vapors escape from the housing onto the door knob.

Callueng, U.S. Pat. No. 6,874,697, discloses a disinfectant dispenser with an electrical pump that sprays disinfectant onto door handles and door knobs when a motion sensor detects movement of a human hand.

Sassoon, U.S. Pat. No. 7,320,418, and Sassoon, U.S. Pat. No. 7,360,674, disclose an aerosol disinfectant can, mounted above a door knob, that sprays disinfectant onto the door knob at timed intervals, not in response to any manual activation.

Stropkay et al., U.S. Pat. No. 7,458,742, discloses a disinfectant dispenser with reservoir mounted adjacent a door handle. Pushing or pulling on a contacting surface of the dispenser causes the dispensing of disinfectant.

Also, GOJO Industries, Inc., located in Akron, Ohio, U.S.A., is known to sell a PURELL® Foaming Hand Sanitizer in a 15 ounce aerosol canister (SKU 9698-12) that is intended for use in a wall-mounted dispenser, which is sold by GOJO Industries under its trademark APX Aerosol Dispensing System (SKU 9699-12). This foaming hand sanitizer aerosol canister, without the wall-mounted dispenser, is suitable for use with the present invention, which is adapted for holding such an aerosol canister.

None of these prior art references, either singly or in combination, discloses or suggests the present invention.

BRIEF SUMMARY OF THE INVENTION

The present invention is a hand sanitizing apparatus adapted for retrofitting use with existing or newly-installed door openers. The apparatus of the present invention is attached to a patient's door in a hospital or clinical setting, and dispenses a hand sanitizing product, such as hand-sanitizing foam, liquid, or gel, such as, for example, PURELL® hand-sanitizing foam, onto the hand of a person opening the patient's door. The apparatus, in large part, substantially blocks access to the lever or handle of the door opener, which is then actuated by the apparatus itself, such that, when the person opening the patient's door engages the paddle of the apparatus with the heel of his or her palm, with an upturned palm and extended fingers, the door is opened and hand-sanitizing product is simultaneously dispensed onto the upturned palm and/or extended fingers, thereby causing the opening of the door and dispensing of hand sanitizing product to be combined into a single action, while the apparatus engages and operates the lever or handle to open the patient's door.

It is an object of the present invention to ensure that hand sanitation occurs each time a person enters a room occupied by a patient, preventing entry to the patient's room unless such hand sanitation has occurred. It is a further object of the present invention to combine into a single action the opening of the door to a patient's room and the dispensing of hand sanitizing product into the hand of the person opening the door. It is a still further object of the present invention to substantially prevent the opening of the door to the patient's room unless hand sanitation has occurred.

BRIEF DESCRIPTION OF THE SEVERAL VIEWS OF THE DRAWING

FIG. 3 is a front view of the present invention in place over a door opener.

FIG. 4 is a right side view of the present invention, taken substantially along the line 4-4 shown in FIG. 3, showing movement of the actuator and door opener handle in dotted outline. The left side view is substantially a mirror image of FIG. 4.

FIG. 5 is a perspective view of the present invention in place over a door opener.

FIG. 6 is a top view of the actuator of the present invention, taken substantially along the line 6-6 shown in FIG. 7.

FIG. 7 is a right side view of the actuator of the present invention. The left side view is substantially a mirror image of FIG. 7.

FIG. 8 is a front view of the actuator of the present invention, taken substantially along the line 8-8 shown in FIG. 7.

FIG. 9 is a side view of one of the pins of the present invention. Both pins are preferably identical to the pin shown in FIG. 9.

FIG. 10 is a side sectional view of the present invention, similar to FIG. 4 but with part of the housing body cut away to show internal structure, and showing a person's palm moving the actuator during opening of the door and dispensing of the hand sanitizing product. The door handle is shown prior to actuation in dotted outline, and the nozzle of the sanitizing canister is shown in dotted outline prior to dispensing of hand sanitizing product.

DETAILED DESCRIPTION OF THE INVENTION

Figure 2:
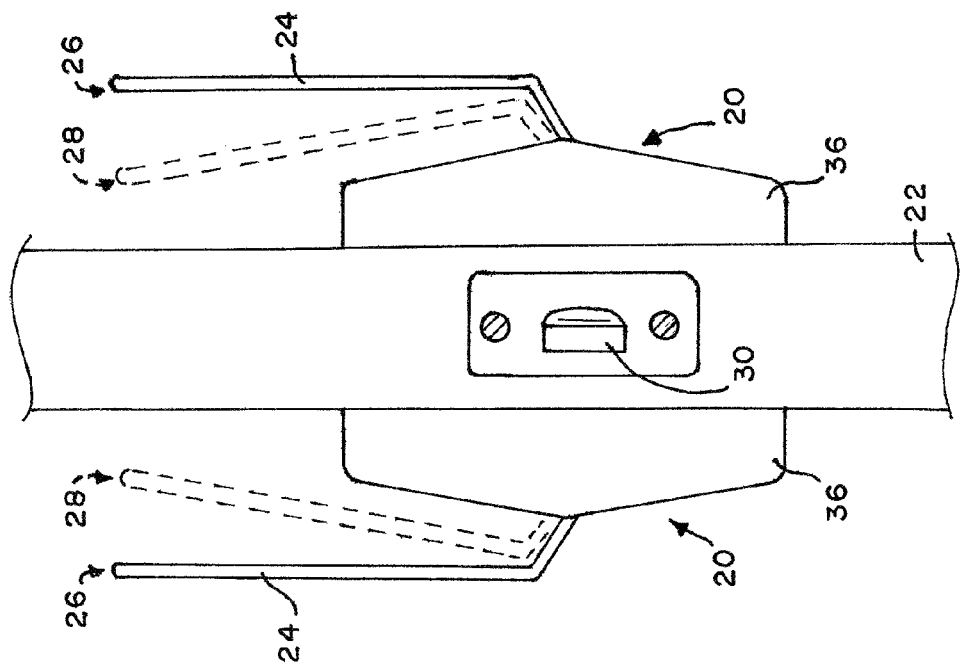
FIG. 2 is a side view of the prior art door opener of FIG. 1, taken substantially along the line 2-2 shown in FIG. 1, and showing a prior art door opener on both the inside and outside surfaces of the same door.
Figure 1:
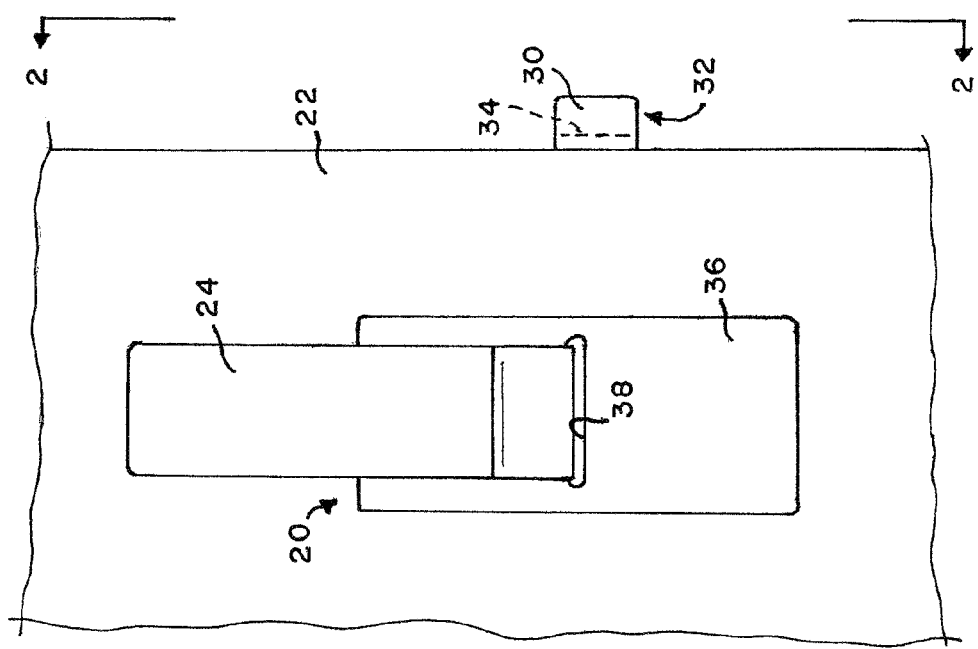
FIG. 1 is a front view of a prior art door opener with which the present invention could be used, shown mounted on a door.
Figure 11:
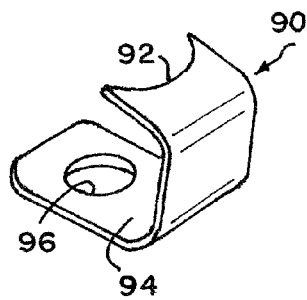
FIG. 11 is a perspective view of the canister holding bracket of the present invention.
Figure 12:
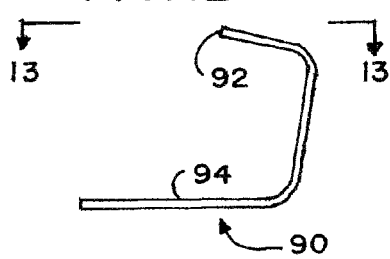
FIG. 12 is a right side view of the canister holding bracket of the present invention.
Figure 15:
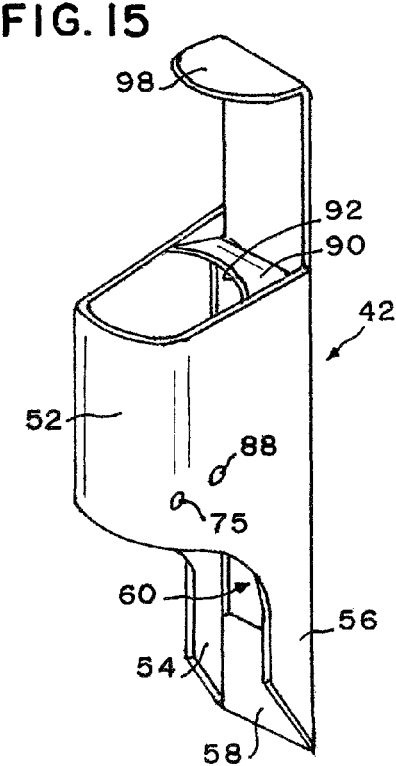
FIG. 15 is a perspective view of the present invention, similar to FIG. 5 but with certain parts removed to show structure that is hidden in FIG. 4.
Figure 13:
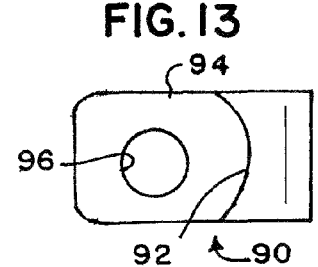
FIG. 13 is a top view of the canister holding bracket of the present invention, taken substantially along the line 13-13 shown in FIG. 12.

Referring to FIGS. 1-2, a well-known prior art door opener 20 is shown mounted to a door 22 to a patient's hospital room or clinic examination room. Door opener 20 has a lever or handle 24 that moves from a first position 26 to a door-opening second position 28 (shown in dotted outline) when contacted by a person opening the door, thereby causing the door latch 30 to reciprocate in a well-known manner from an extended position 32 to a refracted position 34 (shown in dotted outline) so that the door can be opened only when the latch 30 is retracted. Door opener 20 is known to have an internal spring (not shown) that returns handle 24 to first position 26 when the door is not being opened, and which causes the handle 20 to offer some resistance when being pushed as the door is opened. The internal mechanism (not shown) of door opener 20 is typically covered by a shell 36, with handle 24 extending from a slot 38 in shell 36. As shown in FIG. 2, there may be a door opener 20 mounted on both the inside and the outside of door 22.

Referring to FIGS. 2-15, the structure and operation of the hand sanitizing apparatus 40 of the present invention can now be described in detail. It should be noted that apparatus 40 is mounted to door 22 and over door opener 20, heretofore described.

As explained in greater detail hereinbelow, apparatus 40 includes a housing body 42 adapted for receipt about door opener 20, a canister 44 of hand sanitizer received within housing body 42, and an actuator 46 mounted within housing body for movement from a first position 48, shown in solid outline in FIGS. 4 and 5, to a second position 50, shown in dotted outline in FIG. 4 and in solid outline in FIG. 10.

Apparatus 40 substantially limits access to handle 24 by the person opening the door because housing body 42 includes a hood portion 52 and left and right sidewalls 54, 56, with housing body 42 having a back portion 58 with an opening 60 therethrough sized for receipt onto shell 36 of door opener 20. It should be understood that apparatus 40 is preferably securely mounted to door 22 as by well-known screws (not shown) through back portion 58 of housing body 42 and into door 22.

Canister 44 of hand sanitizer is well-known, and is an aerosol canister filled with hand-sanitizing foam, liquid, or gel, such as PURELL®. A suitable aerosol canister 44 for use with the present invention is a 15 ounce aerosol canister (SKU 9698-12) filled with PURELL® Foaming Hand Sanitizer sold by GOJO Industries, Inc., located in Akron, Ohio, U.S.A. Canister 44 has a neck 62 from which a nozzle 64 extends. When nozzle 64 is pushed to one side, as from unpushed position 66 shown in dotted outline in FIG. 10 to pushed position 68 shown in solid outline, pressure within aerosol canister 44 causes hand sanitizing foam 70 to be squirtingly dispensed from canister 44 onto the extended fingers F of a person's upturned palm P, as explained in greater detail hereinbelow.

Actuator 46, mounted within housing body 42, has a hand-contacting portion 72 for contacting the upturned palm P of the person opening the door. Housing body 42 preferably includes an axle 74 to which actuator 46 is mounted, with axle 74 extending through a hole 76 through actuator 46, such that actuator 46 angularly rotates about axle 74 as actuator 46 moves from first position 48 to second position 50. Axle 74 is preferably a cylindrical pin as shown in FIG. 9, which is laser-welded at both ends to hood 52 as through holes 75. Preferably, hand-contacting portion 72 of actuator 46 includes a palm-contacting concave paddle 76 for contacting the heel H of the person's upturned palm P. As best seen in FIGS. 3-5 and 10, paddle 76 further limits access to handle 24 by substantially blocking access to handle 24 by the person opening the door.

Actuator 46 is operably coupled to nozzle 64 of canister 44 and is further operably coupled to handle 24 such that, when actuator 46 is moved from first position 48 to second position 50, handle 24 of door opener 20 becomes moved to door-opening second position 28 as nozzle 64 is caused to dispense hand sanitizer from canister 44.

Actuator 46 preferably includes a nozzle-actuating portion 78 having a nozzle-engaging opening 80 therethrough, and nozzle 64 is inserted through nozzle-engaging opening 80 (compare FIGS. 6 and 10), thereby operably coupling actuator 46 to nozzle 64.

Actuator 46 includes a cam 82, preferably located adjacent a distal end 84 of nozzle-actuating portion 78 of actuator 46, for engageably moving handle 24 into door-opening second position 28 as actuator 46 is moved from first position 48 to second position 50, as best seen in FIG. 10.

Housing body 42 preferably includes a pin 86, preferably of identical construction as axle 74 shown in FIG. 9, which is laser-welded both ends to hood 52 of housing body 42 as through holes 88. Nozzle 64 angularly pivots against pin 86 as actuator 46 moves from first position 48 to second position 50, because of nozzle 64 being inserted through nozzle-engaging opening 80 of nozzle-actuating portion 78 of actuator 46.

Canister 44 is received into housing body 42 and sits against canister holding bracket 90. Bracket 90, which is somewhat "C-shaped" when viewed from either side and which is laser-welded to hood 52 of housing body 42, has a concave first end 92 that rests against the cylindrical body of canister 44. Bracket 90 further has a horizontal portion 94 having a neck-retaining hole 96 therethrough into which neck 62 of canister 44 is received, as best seen in FIG. 10. When canister 44 is inserted into housing body 42, resting against concave first end 92 of bracket 90 and with neck 62 of canister 44 being received into neck-retaining hole 96, canister 44 is held in firmly in position by forwardly-extending lip 98 of the back portion 58 of housing body 42 contacting the bottom 100 of canister 44.

Figure 14:
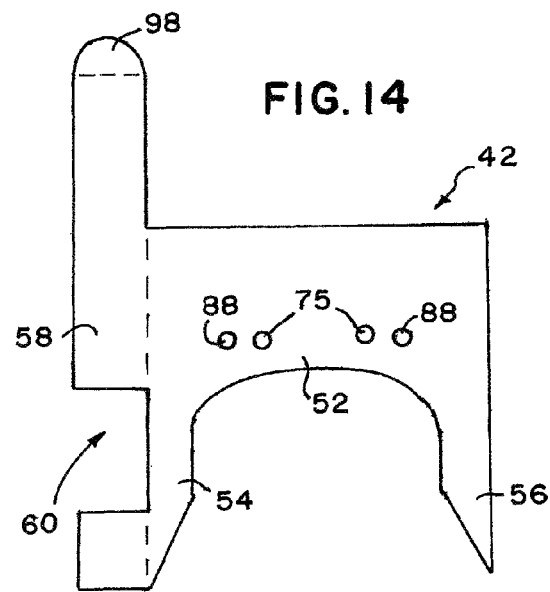
FIG. 14 is a plan view of the housing body of the present invention before bending the housing body into shape.

Referring to FIG. 14, housing body 42 is preferably formed from a single piece of metal as shown, which is folded along fold lines 102 and 104, and hood 52 is formed by putting a curved longitudinal bend in the metal piece.

To install the hand sanitizing door opener apparatus 40 of the present invention, it is mounted to door 22 as by screws (not shown) through back portion 58 into door 22, being received about door opener 20. Canister 44 is inserted into the housing body.

A person desiring to enter the patient's hospital room or clinic room extends an upturned palm, with extended fingers, and contacts the palm-contacting concave paddle 76 with the heel of the upturned palm, as best seen in FIG. 10, pushing paddle 76 toward the door, causing actuator 46 to move from first position 48 to second position 50, thereby causing cam 82 to move door handle 24 into the door-opening second position as actuator 46 pushes nozzle 64 against pin 86 to a tilted or pushed position 68, thereby causing nozzle 64 to dispense hand sanitizing foam into the extended upturned fingers of the person as the door opens. When the person's hand is removed, the internal spring mechanism in the door opener causes the actuator 46 to return to its first position 48, thereby allowing nozzle 64 to return to its unpushed position 66, causing hand sanitizer to cease to be dispensed from nozzle 64.

When canister 44 becomes empty, it can be replaced with another, full, canister.

Although the present invention has been described and illustrated with respect to a preferred embodiment and a preferred use therefor, it is not to be so limited since modifications and changes can be made therein which are within the full intended scope of the invention.

We claim:

1. In combination,
   a door opener having an upwardly-extending lever mounted to a door for pivoting movement with respect thereto, said lever having a distal end remote from the pivoting of said lever, said lever being pivotable from a first lever position to a door-opening second lever position intermediate said first lever position and said door, and
   a hand sanitizing apparatus for sanitizing a person's hand while operating said lever of said door opener, said apparatus comprising:
   (a) housing body, said housing body being adapted for receipt about said distal end of said lever, said apparatus substantially limiting access by said person to said distal end of said lever; and
   (b) a canister of hand sanitizer received into said housing body, said canister having a nozzle extending therefrom for dispensing said hand sanitizer from said canister;
   (c) an actuator mounted within said housing body for movement from a first actuator position to a second actuator position, said actuator having a hand-contacting portion, said hand-contacting portion of said actuator including a palm-contacting paddle; said actuator including a nozzle-actuating portion having a nozzle-engaging opening therethrough, said nozzle being inserted through said nozzle-engaging opening;
   said housing body including a pin against which said nozzle angularly pivots as said actuator moves from said first actuator position to said second actuator position;
   said nozzle-actuating portion of said actuator including a cam for engageably moving said lever into said door-opening second lever position as said actuator is moved from said first actuator position to said second actuator position;
   said housing body including an axle, and said actuator being mounted to said axle for said movement from said first actuator position to said second actuator position, said movement being rotation of said actuator from said first actuator position to said second actuator position;
   said actuator being operably coupled to said nozzle of said canister and further being operably coupled to said lever, such that, when said actuator is moved from said first actuator position to said second actuator position, said lever of said door opener pivots to said door-opening second position as said nozzle is caused to dispense hand sanitizer from said canister.

\* \* \* \* \*